US011974949B2

United States Patent
Keib et al.

(10) Patent No.: US 11,974,949 B2
(45) Date of Patent: May 7, 2024

(54) METHOD FOR SUPPRESSING STRAY LIGHT, LASER-SURGICAL APPARATUS, OPTICAL OBSERVATION DEVICE, AND COMPUTER PROGRAM

(71) Applicant: Carl Zeiss Meditec AG, Jena (DE)

(72) Inventors: Frank Keib, Aalen (DE); Christian Beder, Aalen (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 449 days.

(21) Appl. No.: 17/405,901

(22) Filed: Aug. 18, 2021

(65) Prior Publication Data
US 2022/0054315 A1  Feb. 24, 2022

(30) Foreign Application Priority Data

Aug. 18, 2020 (DE) ...................... 10 2020 121 650.5

(51) Int. Cl.
*A61F 9/008* (2006.01)
*G06T 7/90* (2017.01)

(52) U.S. Cl.
CPC ............ *A61F 9/00823* (2013.01); *G06T 7/90* (2017.01); *A61F 2009/00863* (2013.01)

(58) Field of Classification Search
CPC ....... A61F 9/00823; A61F 2009/00863; G06T 7/90
USPC ......................................................... 382/128
See application file for complete search history.

(56) References Cited

U.S. PATENT DOCUMENTS

| 5,528,426 A | 6/1996 | Howes |
| 5,634,923 A | 6/1997 | Brenner et al. |
| 9,294,656 B2 | 3/2016 | Ikenaga et al. |

(Continued)

FOREIGN PATENT DOCUMENTS

| DE | 4409506 A1 | 9/1995 |
| WO | 2008074057 A1 | 6/2008 |

OTHER PUBLICATIONS

Office Action issued in German Patent Application No. DE 10 2020 121 650.5, dated Apr. 29, 2021 (from which this application claims priority) and English language translation thereof.

*Primary Examiner* — Gabriel I Garcia
(74) *Attorney, Agent, or Firm* — Ewers IP Law PLLC; Falk Ewers (57) ABSTRACT

A laser-surgical apparatus includes a laser emitting laser light with a narrowband wavelength distribution, a digital image sensor or a plurality of digital image sensors that separately record(s) different color channels that represent mutually different spectral wavelength distributions with in each case one maximum corresponding to a specific spectral color and produce(s) separate pieces of image information for the individual color channels, and a graphics module for combining the separate pieces of image information into one color image. In addition, it includes a manipulation module for suppressing the laser light in the color image, which makes it possible to electronically manipulate the pieces of image information of the color channel the spectral wavelength distribution of which has the largest overlap with the narrowband wavelength distribution of the laser light before the separate pieces of image information are combined or during the combining of the separate pieces of image information.

15 Claims, 4 Drawing Sheets

(56) References Cited

U.S. PATENT DOCUMENTS

| | | | |
|---|---|---|---|
| 2005/0181470 A1* | 8/2005 | Bova | G01N 1/44 382/128 |
| 2007/0129709 A1* | 6/2007 | Andersen | A61F 9/00821 606/4 |
| 2008/0167642 A1* | 7/2008 | Palanker | A61F 9/008 606/4 |
| 2010/0128356 A1 | 5/2010 | Feklistov et al. | |
| 2015/0077519 A1 | 3/2015 | Scott et al. | |
| 2015/0309437 A1* | 10/2015 | Otsuka | G03G 21/1666 347/118 |

* cited by examiner

METHOD FOR SUPPRESSING STRAY LIGHT, LASER-SURGICAL APPARATUS, OPTICAL OBSERVATION DEVICE, AND COMPUTER PROGRAM

CROSS REFERENCE TO RELATED APPLICATIONS

This application claims priority to German patent application DE 10 2020 121 650.5, filed Aug. 18, 2020, the entire content of which is incorporated herein by reference.

TECHNICAL FIELD

The present disclosure relates to a method for suppressing stray light with a narrowband wave distribution in a color image. Moreover, the present disclosure relates to a laser-surgical apparatus, to an optical observation device, which can be designed in particular as a surgical microscope, and to a computer-implemented method for suppressing stray light.

BACKGROUND

Laser-surgical apparatuses are widely used in modern medicine. For example, what are known as coagulation lasers, with which for example retinal detachments are treated, are used with increasing frequency in ophthalmology as part of retinal surgery. The lasers used here are typically frequency-doubled Nd:YAG lasers having a laser wavelength of 532 nm. This wavelength lies in the green wavelength range and is greatly absorbed by the human retina. For this reason, such a laser can be used to very easily deposit a large amount of energy in the retina, which ultimately results in the destruction of the relevant retina regions, but also in the fusion of these retina regions with the underlying tissue (what is known as coagulation). In this way, at least further detachment of adjacent but not yet detached parts of the retina is then prevented.

Since the lasers used have powers of up to a few watts, the physician and all people involved in the operating theater must be protected against the laser light. While all others can be protected with conventional laser safety goggles, the treating physician should continue to be able to see through the microscope during treatment. For this reason, the physician has so far been protected by a laser safety filter mounted inside the tube. Such laser safety filters, which can also be designed so as to be able to be pivoted in and out, are described, for example, in U.S. Pat. No. 5,528,426 B and in DE 44 09 506 A1. While the laser safety filters described in those two documents are based on absorption of the laser wavelength, laser safety filters based on reflection of the laser wavelength also exist. By way of example, such a laser safety filter is described in WO 2008/074057 A1. In both cases, laser light can be blocked with an optical density OD 4 or above. This means that the intensity of the laser light downstream of the filter is attenuated to at most $1 \times 10^{-4}$ of the intensity upstream of the filter. In other words, the laser safety filter reduces the intensity of the laser light passing through it by at least a factor of 10000.

In addition to the coagulation laser, the laser apparatuses used in eye surgery frequently also have what is known as a target laser, which has a laser wavelength that generally lies in the red wavelength range. This target laser is used to target the section of the retina that is to be coagulated. The laser light of the target laser has a significantly lower intensity than the laser light of the coagulation laser, not only so as not to endanger the patient or the physician, but to also enable observation of the retina without overexposure due to the laser radiation of the target laser in the case of an active target laser, because targeting using the target laser is possible only then.

Such laser-surgical apparatuses generally include surgical microscopes that not only enable observation of the operating region through eyepieces but in addition can also record the surgical procedure with a digital camera and present it on a monitor. During the time in which the coagulation laser is activated, the intensity of the green laser light is generally so high that the green laser light completely overexposes the image recorded with the digital camera. Since generally very many points are treated with the coagulation laser in short succession, the video image then resembles a stroboscope recording more than a video sequence, because neither the dynamics nor the switching times of current camera sensors are able to compensate for this enormous, momentary brightness difference.

As long as the video image serves only for documenting purposes, the overexposure of the image recorded with the digital camera does not pose a major problem. However, the overexposure becomes a problem when the video image is the main type of visualization for the physician, in other words when the physician observes the operating region on a monitor during the treatment rather than through the eyepieces of a surgical microscope. It is also possible for a laser safety filter to be fixedly mounted in such a surgical microscope in order to protect the camera, with the laser safety filter then fulfilling the same function as the physician's safety filter, although in this case it is not the eyes of the treating physician that are protected against the harmful laser light, but a camera sensor is protected against overexposure. However, this functionality in laser safety filters based on selective reflection of the laser light results in reflections of the laser light, that is to say green reflections, appearing in the camera image, even during normal operation without the coagulation laser being switched on. For this to occur, it merely takes a sufficiently strong, individual light distribution in the object, which comes about for example from a reflection of the illumination. Such reflections can arise for example owing to a liquid level, an interface with a large change in the refractive index, for example if there is air in the eye, or from plain instruments.

The problems mentioned could be realized for example by improving the laser safety filter by steeper edges between the wavelength range surrounding the laser wavelength and the remaining wavelength ranges. However, this makes the filter very complicated and expensive. Another possibility for overcoming the abovementioned problem would be to tilt a reflective laser safety filter in the beam path of the surgical microscope to such an extent that the reflections described are reflected so obliquely that they are no longer incident on the camera sensor. However, reflective camera safety filters have a specific thickness that would have to be reduced if the filter were to have a relatively strongly inclined position, since only a thin filter and not a thick filter can be tilted without negative consequences for the imaging performance. Since the filter coating is additionally very thick and has strong stresses, the thin filter would need a counter-coating to prevent it from being bent, because the imaging performance would otherwise in turn be negatively affected. In addition, the properties of the filter coating would also have to be adapted to the oblique incidence of the laser light. All of this increases the complexity of the reflective laser safety filter and consequently the costs of producing it. Moreover, a tilted reflective laser safety filter requires more installation space in the surgical microscope, which is not always easy to implement. Problems associated with the inclined position of the reflective laser safety filter could be avoided by the laser safety filter being cut in half obliquely at the center, the filter coating being applied there, and the two halves then being placed back together, which would likewise result in the reflections no longer arriving at the camera sensor. However, this would also greatly increase the complexity of the reflective laser safety filter, because both the oblique incidence of the laser light and the use of the filter coating in the glass of the laser safety filter would require the construction of the filter coating to involve even more individual layers. This solution would therefore become highly complex and very expensive.

SUMMARY

It is therefore a first object of the present disclosure to provide a method for suppressing stray light with a narrowband wavelength distribution in a color image recorded with a digital image sensor, which method can be implemented cost-effectively with simple means.

It is a second object of the present disclosure to provide a laser-surgical apparatus and an optical observation device with a digital image sensor, in which it is possible to suppress stray light with a narrowband wavelength distribution with simple and cost-effective means.

The first object is achieved by a method for suppressing stray light with a narrowband wavelength distribution in a color image, and the second object is achieved by a laser-surgical apparatus and an optical observation device as described herein.

In the method according to the disclosure for suppressing stray light with a narrowband wavelength distribution with a color image, the color image is recorded with a digital image sensor or a plurality of digital image sensors. The digital image sensor, or the digital image sensors, separately record(s) different color channels that represent mutually different spectral wavelength distributions with, in each case, a maximum corresponding to a specific spectral color, and produce(s) separate pieces of image information for the individual color channels. This can be accomplished for example in that the beam path is divided, for example with a prism, into three beam paths with the mutually different wavelength distributions and the beam paths are each fed to separate image sensors. However, it is also possible to realize the separate recording of the different color channels using a single image sensor, if what is known as a Bayer matrix, which arranges a filter that only allows through one of the mutually different spectral wavelength distributions upstream of each pixel, is arranged upstream of the image sensor. In both cases, the digital image sensor, or the digital image sensors, is/are used to produce pieces of image information that are separate for the individual color channels and to generate the color image by combining the separate pieces of image information. According to an aspect of the disclosure, the stray light is suppressed by electronically manipulating the pieces of image information of the color channel whose spectral wavelength distribution has the greatest overlap with the narrowband wavelength distribution of the stray light before the separate pieces of image information are combined or during the combining of the separate pieces of image information. In other words, the stray light is suppressed by manipulating the data representing the pieces of image information.

The method according to the disclosure represents a cost-effective and simple (in terms of its production) solution for avoiding overexposures of a digital color image by stray light, which additionally renders mechanically complex pivot apparatuses redundant. Since in the case of purely digital optical observation devices such as purely digital surgical microscopes additionally no installation space for laser safety filters is required, the solution according to the disclosure can also be used in highly compact optical observation devices, or the latter can have a highly compact design. In addition, reflections in the image recorded with the digital camera can be avoided as compared to the use of an in particular reflective laser safety filter.

In a particularly simple design of the method according to the disclosure, the electronic manipulation of the pieces of image information involves that the pieces of image information of the color channel whose spectral wavelength distribution has the greatest overlap with the narrowband wavelength distribution of the stray light are not included at all, or are included with a reduced weighting compared to the pieces of image information of the remaining color channels, in the color image during the generation of the color image. This solution requires a particularly low computational outlay and thus makes it possible to switch particularly quickly from a non-manipulated color image to a manipulated color image. If the pieces of image information are included in the color image but with a reduced weighting, overexposures of the color image due to the stray light can be avoided without a piece of information that may be present in the stray light being lost completely. If the stray light is caused for example by a laser pulse of a treatment laser, it is advantageous if the treating physician is still able to identify, despite the reduction in the stray light, the location of the treatment region at which the laser pulse has arrived.

Not taking account, or taking account with reduced weighting, of pieces of image information of the color channel whose spectral wavelength distribution has the greatest overlap with the narrowband wavelength distribution of the stray light, however, results in a falsification of the colors in the color image. Such a falsification can be partially compensated for if the electronic manipulation of the pieces of image information involves the at least partial replacement of the pieces of image information of the color channel whose spectral wavelength distribution has the greatest overlap with the narrowband wavelength distribution of the stray light with pieces of image information of at least one of the remaining color channels. For example, if the stray light lies in the green spectral range and the color channel representing the green wavelength distribution is not included, or is included only with reduced weighting, in the color image, it is possible to partially compensate for the associated color falsification by at least partially replacing the removed pieces of image information of the green color channel with pieces of image information of the blue color channel. Although color falsifications can in this way be partially compensated for, the color presentation can be adapted to the original color presentation even better if the electronic manipulation of the pieces of image information involves assigning the pieces of image information of at least one of the color channels a color that deviates from the color corresponding to the maximum of its spectral wavelength distribution during the generation of the color image. For example, the maximum of the spectral wavelength distribution of the blue color channel corresponds to a blue color. If this blue color is replaced by the color cyan during the generation of the color image, a largely realistic color impression can be restored, in particular, if additionally the pieces of image information that are missing in the green color channel have been at least partially replaced by pieces of image information of the blue color channel. If the pieces of image information of the color channel whose spectral wavelength distribution has the greatest overlap with the narrowband wavelength distribution of the stray light are included in the color image with a reduced weighting compared to the pieces of image information of the remaining color channels during the generation of the color image, it is advantageous if the color manipulation is effected such that the stray light reduced in the image stands apart from other light, for example from the light that is reflected by the treatment region and/or from the light of a target laser.

If the method according to the disclosure is to be used in eye surgery with regard to the coagulation of the retina, the narrowband wavelength distribution of the stray light frequently has a maximum in the green wavelength range. Typically, the digital image sensor or the digital image sensors here record(s) separate pieces of image information for at least three different color channels, wherein a first one of the color channels is a red color channel whose spectral wavelength distribution has a maximum representing a red color, a second one of the color channels is a green color channel whose spectral wavelength distribution has a maximum representing a green color, and a third one of the color channels is a blue color channel whose spectral wavelength distribution has a maximum representing a blue color. In this configuration of the method, the pieces of image information of the second color channel are electronically manipulated. In this way, overexposure of the color image due to the green laser light of the coagulation laser can be avoided. The electronic manipulation of the pieces of image information can here in particular involve that the pieces of image information contained in the green color channel are not included at all, or are included with a reduced weighting compared to the pieces of image information of the red color channel and the blue color channel, in the color image during the creation of the color image. The resulting color falsification can be at least partially compensated for in that the electronic manipulation of the pieces of image information involves at least partially replacing the pieces of image information contained in the green color channel with pieces of image information of the blue color channel. Moreover, color falsifications can be corrected if the electronic manipulation of the pieces of image information includes assigning pieces of image information of at least the red or the blue color channel a color that deviates from the red or blue color represented by the maximum of the respective spectral wavelength distribution during the generation of the color image. For example, rather than the color blue, the color cyan can be assigned to the pieces of image information of the blue color channel, as a result of which, in particular in combination with the at least partial replacement of the pieces of image information of the green color channel with pieces of image information of the blue color channel, a nearly color-true presentation of the color image can be achieved, as would occur without overexposure due to the green light of the coagulation laser.

To avoid incorrect operation of an apparatus performing the method according to the disclosure, resulting in a false-color presentation although no stray light is present, the method can be developed such that an alert is issued at least if the electronic manipulation of the pieces of image information is active and there is no stray light. For example, the alert can be included in the color image itself in the form of a boundary designed to be easily perceivable of the color image displayed or in the form of a symbol that is easy to perceive in the peripheral region of the color image and represents an indication of the active manipulation. However, it is also possible to realize the alert in the form of a warning sound or of a display of the apparatus performing the method. With the alert, it is easy for a user of the apparatus to notice that a false-color presentation is present and to terminate the electronic manipulation, if this is not required. In this case, it is in particular also possible, as part of the method, to check whether a stray-light-producing unit is active, to check whether the electronic manipulation of the pieces of image information of the color channel whose spectral wavelength distribution has the greatest overlap with the narrowband wavelength distribution of the stray light is active; and to issue an alert if the check shows that a stray-light-producing unit is not active and the electronic manipulation of the pieces of image information is active.

In this way it is possible to ensure that the alert is issued only if the electronic manipulation of the pieces of image information is active even though there is no stray light. However, it is also possible to issue the alert for as long as the electronic manipulation of the pieces of image information is active, independently of whether or not stray light is present.

According to a further aspect of the disclosure, a laser-surgical apparatus is provided. Said apparatus includes:

A laser emitting laser light with a narrowband wavelength distribution. Due to its high intensity, the laser light represents stray light in a color image recorded of the region illuminated with the laser light.

A digital image sensor or a plurality of digital image sensors that separately record(s) color channels that represent mutually different spectral wavelength distributions with in each case one maximum corresponding to a specific spectral color and produce(s) separate pieces of image information for the individual color channels. The digital image sensor or the plurality of digital image sensors can be part of a digital camera or part of another apparatus that is suitable for image recording.

A graphics module for combining the separate pieces of image information into one color image. The graphics module can be a hardware module or a software module of a camera. Alternatively, it may also be a hardware module or software module of another apparatus suitable for image recording or of a computer (e.g., a graphics card) to which the digital image sensor or the plurality of digital image sensors is or are connected.

According to an aspect of the disclosure, the laser-surgical apparatus additionally includes a manipulation module for suppressing the laser light in the color image, which makes it possible to electronically manipulate the pieces of image information of the color channel whose spectral wavelength distribution has the greatest overlap with the narrowband wavelength distribution of the laser light before the separate pieces of image information are combined or during the combining of the separate pieces of image information. In other words, the manipulation module for suppressing the stray light is designed to manipulate the data representing the pieces of image information. In such a laser apparatus, an overexposure of the color image due to the laser light can be prevented. For this reason, the manipulation module for suppressing the laser light can make electronic manipulation of the pieces of image information possible in a manner such that those of the color channel whose spectral wavelength distribution has the greatest overlap with the narrowband wavelength distribution of the laser light are not included at all, or are only included with a reduced weighting compared to the pieces of image information of the remaining color channels, in the color image during the creation of the color image. Any color falsifications occurring here in the color image can be compensated for at least partially by the manipulation module for suppressing the laser light making possible electronic manipulation of the pieces of image information such that the pieces of image information of the color channel whose spectral wavelength distribution has the greatest overlap with the narrowband wavelength distribution of the laser light are replaced at least partially with pieces of image information of one of the remaining color channels. Additionally or alternatively, it is possible for compensating color falsifications that the graphics module makes electronic manipulation of the pieces of image information possible in a manner such that the pieces of image information of at least one of the color channels are assigned a color that deviates from the color corresponding to the maximum of its spectral wavelength distribution during the generation of the color image.

Although it is possible in principle that the suppression of the laser light in the generated color image is activated by the staff inside the operating theater before a laser pulse takes place, it is desirable to let the activation of the suppression of the laser light be performed automatically, for example to be able to implement faster pulse sequences and to counteract human failure. For this purpose, the laser-surgical apparatus in a further configuration includes a communication module that is connected at least to the laser and to the manipulation module and is configured to transmit a switch-on signal to the manipulation module when the laser is switched on. In addition, the manipulation module in this configuration is configured to start the electronic manipulation of the pieces of image information upon receipt of the switch-on signal. The electronic manipulation of the pieces of image information can then be terminated in different ways. For example, it is possible for the staff in the operating theater to terminate the suppression of the laser light by the electronic manipulation of the pieces of image information for example by entering a corresponding command into a computer or by pressing a key of the laser-surgical apparatus. However, the termination of the electronic manipulation of the pieces of image information preferably also takes place in an automated manner. For this purpose, it is possible to use for example the actuation signal for laser safety filters that is frequently provided by ophthalmological lasers. In a first development of the described configuration of the laser-surgical apparatus, the communication module is then additionally designed to transmit a switch-on duration to the manipulation module in addition to the switch-on signal. The switch-on duration in this case indicates how long the laser remains switched-on once it has been switched on. In this development, the manipulation module is additionally designed to terminate the electronic manipulation of the pieces of image information after the switch-on duration has expired. In an alternative development of the described configuration, the communication module is designed to transmit a switch-off signal to the manipulation module when the laser is switched off. In this development, the manipulation module is configured to terminate the electronic manipulation of the pieces of image information upon receipt of the switch-off signal. Both developments make it possible to begin and to terminate the electronic manipulation of the pieces of image information in an automated manner. If a color that deviates from the color corresponding to the maximum of its spectral wavelength distribution is to be assigned to one of the color channels, the communication module is also connected to the graphics module and is configured to also transmit the switch-on signal to the graphics module when the laser is switched on. In this development, the graphics module is then at least designed to begin the deviating assignment of the color upon receipt of the switch-on signal and, if a switch-on duration or a switch-off signal is transmitted, to terminate the deviating assignment of the color after the switch-on duration has expired or upon receipt of the switch-off signal.

In an advantageous development, the laser-surgical apparatus includes a warning module that issues an alert at least if the manipulation module is active without the laser being active. The alert can, however, also be permanently active as long as the manipulation module is active, that is to say independently of whether or not the laser is active. The warning module can be, for example, part of the manipulation module or part of the graphics module and can cause the respective module to display the alert in the color image itself in the form of a boundary designed to be easily perceivable of the color image displayed or in the form of a symbol that is easy to perceive in the peripheral region of the color image and represents an indication of the active manipulation. However, it is also possible that the manipulation module or the graphics module is connected to the laser-surgical apparatus and activates a loudspeaker or a light-emitting indicator of the laser-surgical apparatus to produce an acoustic or visual alert. If the warning module is not part of the manipulation module, it can receive therefrom a signal indicating the activity of the manipulation module. With the alert, it is easy for a user of the apparatus to notice that a false-color presentation is present and to terminate the electronic manipulation, if this is not required. It is particularly advantageous if the warning module checks whether the laser is active, checks whether the manipulation module is active, and issues the alert if the check shows that the laser is not active and the manipulation module is active. In this way, the alert can be limited to those time periods in which the manipulation module is active even though no laser light is present.

According to yet a further aspect of the present disclosure, an optical observation device is provided, which can in particular be a surgical microscope. Said observation device includes:

- a digital image sensor or a plurality of digital image sensors that separately record(s) different color channels that represent mutually different spectral wavelength distributions with in each case one maximum corresponding to a specific spectral color and produce (s) separate pieces of image information for the individual color channels, and
- a graphics module for combining the separate pieces of image information into one color image.

The digital image sensor or the plurality of digital image sensors can, in particular, be part of a digital camera of the optical observation device.

The optical observation device according to the disclosure additionally includes a manipulation module for suppressing stray light with a narrowband wavelength distribution in a color image. The manipulation module makes it possible to electronically manipulate the pieces of image information of the color channel whose spectral wavelength distribution has the greatest overlap with the narrowband wavelength distribution of the stray light before the pieces of image information are combined or during the combining of the pieces of image information. In other words, the manipulation module for suppressing the stray light is configured to manipulate the data representing the pieces of image information.

In such an optical observation device, it is possible to dispense with a laser safety filter in the beam path extending to the digital image sensor or to the digital image sensors. If the optical observation device moreover has an observation beam path extending to at least one eyepiece, a laser safety filter can still be present therein in order to protect the treating physician. In the case of a purely digital optical observation device in which the visualization is realized only using displays, it is possible, by contrast, to entirely dispense with a laser safety filter.

In the optical observation device according to the disclosure, the manipulation module for suppressing the stray light can in particular make electronic manipulation of the pieces of image information possible in a manner such that the pieces of image information of the color channel whose spectral wavelength distribution has the greatest overlap with the narrowband wavelength distribution of the stray light are not included at all, or are included with a reduced weighting compared to the pieces of image information of the remaining color channels, in the color image during the creation of the color image. Any color falsifications occurring here can be compensated for, for example, by the manipulation module for suppressing the stray light making possible electronic manipulation of the pieces of image information such that the pieces of image information of the color channel whose spectral wavelength distribution has the greatest overlap with the narrowband wavelength distribution of the stray light are replaced at least partially with pieces of image information of at least one of the remaining color channels. Additionally or alternatively, it is possible for compensating color falsifications that, for suppressing the stray light, the graphics module makes electronic manipulation of the pieces of image information possible in a manner such that the pieces of image information of at least one of the color channels are assigned a color that deviates from the color corresponding to the maximum of its spectral wavelength distribution during the generation of the color image. The optical observation device according to the disclosure can be used as an optical observation device in the laser-surgical apparatus according to an aspect of the disclosure. Typically, it is designed as a surgical microscope.

According to yet a further aspect of the present disclosure, a computer-implemented method for suppressing stray light with a narrowband wavelength distribution in a color image, which is represented by separate pieces of image information for different color channels that represent mutually different spectral wavelength distributions with in each case one maximum corresponding to a specific spectral color, is provided. The computer-implemented method includes the steps of:

receiving separate pieces of image information, and
generating the color image by combining the separate pieces of image information.

According to an aspect of the disclosure, the stray light is suppressed by electronically manipulating the pieces of image information of the color channel whose spectral wavelength distribution has the greatest overlap with the narrowband wavelength distribution of the stray light before the separate pieces of image information are combined or during the combining of the separate pieces of image information. In other words, the stray light is suppressed by manipulating the data representing the pieces of image information. The computer-implemented method according to an aspect of the disclosure can be further embodied like the previously described method for suppressing stray light.

According to yet a further aspect of the present disclosure, a computer program for suppressing stray light with a narrowband wavelength distribution in a color image, which is represented by separate pieces of image information for different color channels that represent mutually different spectral wavelength distributions with in each case one maximum corresponding to a specific spectral color, is provided. The computer program includes instructions that, when they are executed on a computer, cause the computer to receive the separate pieces of image information and to combine the separate pieces of image information to generate the color image. According to an aspect of the disclosure, the computer program additionally includes instructions that, when they are executed on a computer, cause the computer to electronically manipulate, for suppressing the stray light, the pieces of image information of the color channel whose spectral wavelength distribution has the greatest overlap with the narrowband wavelength distribution of the stray light before the separate pieces of image information are combined or during the combining of the separate pieces of image information. In other words, the stray light is suppressed by manipulating the data representing the pieces of image information. The computer-implemented method according to an aspect of the disclosure can be developed to carry out the developments of the previously described method for suppressing stray light.

BRIEF DESCRIPTION OF THE DRAWINGS

The disclosure will now be described with reference to the drawings wherein.

DESCRIPTION OF EXEMPLARY EMBODIMENTS

The disclosure will be described below in detail on the basis of exemplary embodiments for explanatory purposes. However, it is clear to a person skilled in the art that the exemplary embodiments show merely selected possibilities from a large number of possibilities for realizing the present disclosure, and modifications of the exemplary embodiments are therefore possible within the scope of the disclosure. Therefore, the present disclosure is not intended to be limited by the exemplary embodiments that follow but rather only by the appended claims.

Figure 1:
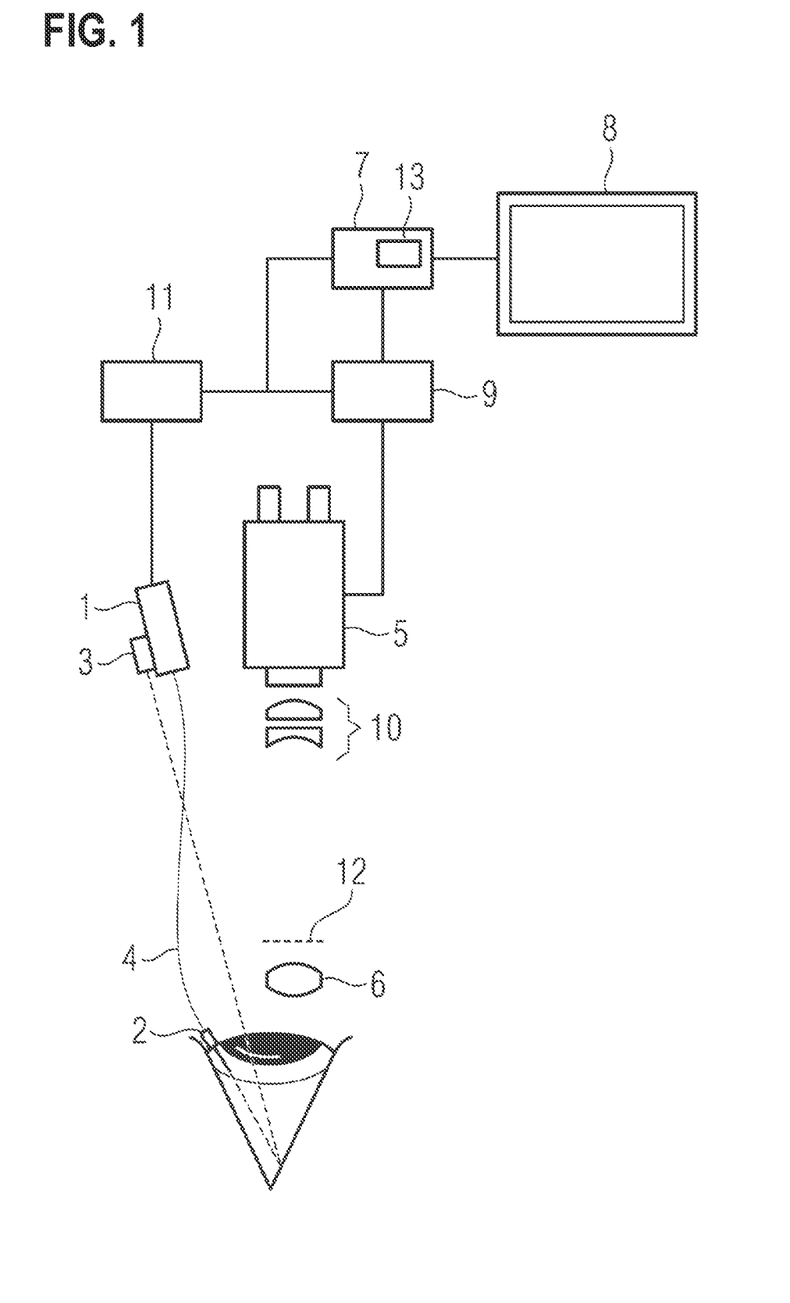
FIG. 1 shows a schematic illustration of components for a laser-surgical apparatus according to an exemplary embodiment of the disclosure.

FIG. 1 schematically shows an exemplary embodiment of a laser-surgical apparatus. The laser-surgical apparatus of the present exemplary embodiment is designed as an apparatus for posterior-segment eye surgery and can be used in particular to treat retinal detachments. The apparatus includes a coagulation laser 1, which in the present exemplary embodiment is embodied in the form of a frequency-doubled Nd:YAG laser having a wavelength of 532 nm. The spectral wavelength distribution of the laser light is very narrow with a maximum at the aforementioned 532 nm. The maximum represents a green spectral color. To treat retinal detachments, the affected location of the retina is irradiated with the laser light, as a result of which the retinal tissue is ultimately destroyed on account of the energy introduction, but the retinal tissue is at the same time also fixedly connected to the tissue that is located more deeply, which is referred to as coagulation. The power of the coagulation laser lies somewhere in the range of up to a few watts. The radiation with the laser light of the coagulation laser 1 is effected in the present exemplary embodiment as part of the endoillumination. For this purpose, the laser light is coupled into an optical fiber 4, which is introduced into the eye via a trocar 2 that has been placed into the eye through the sclera, in order to radiate the retina with the laser light from the inside of the eye.

In addition, the laser-surgical apparatus includes a target laser 3, the laser radiation of which frequently has a maximum in the red wavelength range and in which the intensity of the laser radiation is generally significantly lower than the intensity of the laser radiation of the coagulation laser 1. The intensity of the laser radiation of the target laser must here be significantly weaker than the intensity of the laser radiation of the coagulation laser so that neither the patient nor the physician is injured and so that, in addition, the target laser does not overexpose the ocular fundus, with the result that the point of incidence of the target laser on the ocular fundus is clearly visible. The target laser is used to target the location of the retina that is to be treated, and the coagulation laser is then initiated.

Figure 2:
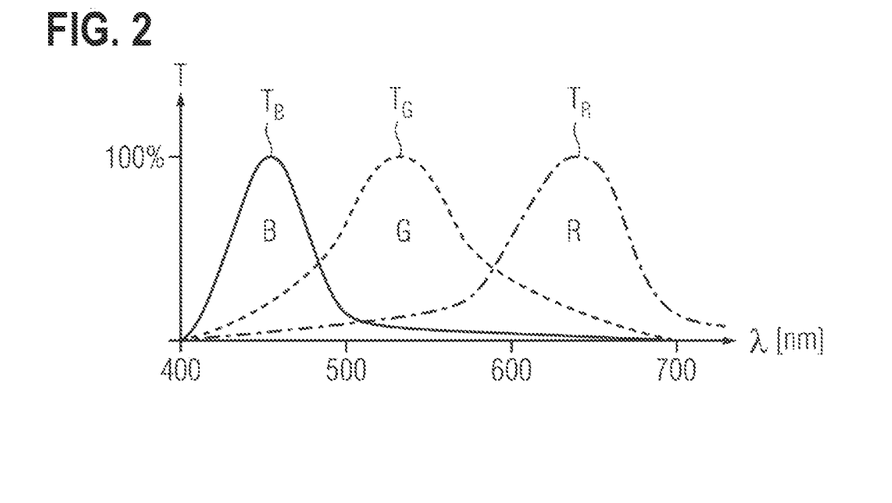
FIG. 2 shows the transmission properties of elements defining the color channels.

In order to view the ocular fundus during the treatment, the laser-surgical apparatus in the present exemplary embodiment includes a surgical microscope 5, which is configured to view the ocular fundus using an ophthalmic loupe 6. The ophthalmic loupe 6 here produces an intermediate image 12 of the ocular fundus. The intermediate image 12 can here be focused in the surgical microscope 5 with an optics group 10. In addition, the surgical microscope 5 is equipped with at least one digital image sensor with which a digital color image of the ocular fundus, which is then displayed on a monitor 8, is recorded. In the present exemplary embodiment for the laser-surgical apparatus, at least one image sensor having a Bayer matrix is present, with the aid of which it is possible to assign each pixel of an image sensor in each case one specific color channel that represents a spectral wavelength distribution with a specific maximum. In the present exemplary embodiment, each pixel is supplied in each case with light of one of three color channels. For this purpose, the Bayer matrix arranged upstream of the sensor has spectral filters that let respectively other spectral wavelength ranges through. In the present exemplary embodiment, three different types of spectral filters are present, wherein the first type defines a first color channel R by it having a filter characteristic that lets a spectral wavelength distribution with a maximum in the red wavelength range through, the second type defines a second color channel G by it letting a spectral wavelength distribution with a maximum in the green spectral range through, and the third type defines a third color channel B by it letting a spectral wavelength distribution with a maximum in the blue spectral range through. An example of the transmission curves TR, TG and TB of the red spectral filters, the green spectral filters, and the blue spectral filters of the Bayer matrix representing elements defining the color channels are illustrated schematically in FIG. 2, which shows the transmission curves TR, TG and TB of the three spectral filters in each case as a function of the wavelength λ. The pixels assigned to the respective filters then convert the light that is incident thereon into electrical signals that serve as pieces of image information for the individual color channels. In this way, separate pieces of image information are produced for all color channels.

In an alternative configuration, it is possible to use three image sensors rather than a single image sensor with a Bayer filter, wherein in each case one image sensor is present for each color channel in that case. Using a color splitter system comprising prisms, the light reflected by the object is then split into three spectral wavelength distributions, of which one has a maximum in the red spectral range, the other has a maximum in the green spectral range, and the last one has a maximum in the blue spectral range. For this purpose, the color splitter system has spectral transmission properties that resemble the spectral transmission properties of the filters of the Bayer matrix illustrated in FIG. 2. The separated wavelength distributions are then supplied to the different image sensors. Compared to an image sensor with a Bayer matrix, this offers the advantage that in each case all the pixels of an image sensor are used to produce the pieces of image information of a color channel and, consequently, the maximum resolution of the image sensors can be utilized. In the case of an image sensor with a Bayer matrix, by contrast, the pixels of the image sensor are distributed over the three color channels such that the pieces of image information produced for the three color channels have a lower resolution than would be possible in principle with the number of pixels of the image sensor.

To illustrate the images recorded with the image sensor or the image sensors of the surgical microscope 5, a graphics module 7 is present in the present exemplary embodiment, which combines the separate pieces of image information and thus generates a color image that is finally displayed on a monitor 8 or on another type of display. The graphics module 7 can be integrated as software or hardware in the surgical microscope 5, can be implemented by software executed on a computer and/or by the graphics card of a computer, or can be implemented as a dedicated software or hardware module of the laser-surgical apparatus.

When the coagulation laser 1 is activated, the intensity in the green color channel is very much higher than in the other two color channels. When the separate pieces of image information of the three color channels are combined, this results in the green color channel being so dominant that the green spectral range in the color image completely overexposes the other spectral ranges. Since it is possible with the coagulation laser 1 to generally coagulate very many points of the retina in quick succession, the video sequence recorded with the at least one digital image sensor resembles a stroboscope recording because neither the dynamics nor the switching times of the at least one digital image sensor are capable of compensating for the enormous momentary brightness difference. In order to prevent overexposure of the red and blue color channels by the green color channel in the color image, a manipulation module 9 for suppressing the stray-light-forming laser light in the color image is connected in the present exemplary embodiment upstream of the graphics module 7. Said manipulation module 9 makes it possible to electronically manipulate the pieces of image information of the green color channel, that is to say to manipulate the data representing the pieces of image information, before the pieces of image information are combined. In the present exemplary embodiment, the electronic manipulation is effected such that the pieces of image information or the data of the green color channel are not transmitted to the graphics module 7. Rather, the manipulation module 9 duplicates the pieces of image information of the blue color channel and transmits them to the graphics module 7 both as pieces of image information of the blue color channel and as pieces of image information of the green color channel. Although it is in principle also possible to remove the pieces of image information of the green color channel without replacing them, this results in a significant color falsification in the color image. These color falsifications can be reduced if the pieces of image information of the blue color channel are also transmitted to the graphics module 7 as the pieces of image information of the green color channel. The manipulation module 9 for suppressing the stray light can be integrated, for example, as software or hardware in the surgical microscope 5, can be implemented by software executed on a computer or can be implemented as a dedicated software or hardware module of the laser-surgical apparatus. It is also possible in this case that the graphics module 7 and the manipulation module 9 for suppressing the stray light are integrated as submodules in a hardware or software module.

Even if the duplication of the pieces of image information of the blue color channel and the transmission of the duplicated pieces of image information as pieces of image information of the green color channel make a significantly more realistic color presentation possible than if the pieces of image information of the green color channel were to be removed without being replaced, a residual color falsification still remains in the color image. Due to the fact that the same pieces of image information are present both in the green and in the blue color channel, a purely blue color of the object in the color image would be represented by a mixture of blue and green, that is to say a purely blue color is presented in the color image as cyan. This color error can be compensated for by the color presentation on the monitor being electronically manipulated in the graphics module 7, specifically such that the color cyan is presented on the monitor as pure blue. In addition, it is possible in the present exemplary embodiment to allow the presentation of the color red in the monitor presentation by a red that has shifted into orange, as a result of which it is possible overall to achieve a more realistic color presentation despite the absence of the pieces of image information of the green color channel.

In the present exemplary embodiment, the pieces of image information of the green color channel are not transmitted by the manipulation module 9 to the graphics module 7. If the locations of incidence of the laser light on the retina are to be noticeable during the coagulation treatment, it is, however, also possible to transmit the green color channel with a reduced weighting to the graphics module 7, as a result of which the points of incidence of the laser light of the coagulation laser 1 light up orange in the color image without overexposing the entire color image. During the manipulation of the color presentation on the monitor 8 by way of the graphics module 7, care should be taken that the color of the laser light in the color image remains distinguishable from the red color of the target laser 3.

As already explained, during the treatment of the retina, very many points are treated with the coagulation laser 1 in short succession, wherein the coagulation laser 1 emits short pulses of laser light in quick succession. The electronic manipulation of the pieces of image information for suppressing the laser light in the color image is to take place here over the time period in which the sequence of laser pulses is emitted and can be interrupted between the individual laser pulses of the sequence. For this purpose, the laser-surgical apparatus has a communication module 11, which is connected both to the coagulation laser 1 and to the manipulation module 9 and which transmits a switch-on signal to the manipulation module 9 when the laser 1 is switched on. In addition, it transmits a switch-off signal to the manipulation module 9 when the coagulation laser 1 is switched off. When the switch-on signal is received, the manipulation module 9 begins the electronic manipulation of the pieces of image information of the green color channel, while it terminates the electronic manipulation of the pieces of image information of the green color channel when the switch-off signal is received. In the present exemplary embodiment, in which it is also possible to manipulate the color presentation on the monitor 8 with the aid of the graphics module 7, the switch-on signal and the switch-off signal are additionally also transmitted from the communication module 11 to the graphics module 7, which begins the manipulation of the color presentation on the monitor 8 upon receipt of the switch-on signal and terminates the manipulation of the color presentation on the monitor 8 when it receives the switch-off signal from the communication module 11.

Although, in the present exemplary embodiment, a switch-on signal and a switch-off signal are output by the communication module 11 to the manipulation module 9 and to the graphics module 7, it is also possible that the communication module 11 transmits a switch-on signal together with a switch-on duration, rather than a switch-on signal and a switch-off signal, to the manipulation module 9, and, if the graphics module 7 is to manipulate the color presentation on the monitor 8, to the graphics module 7. However, it is also possible in principle to manually initiate the start of the electronic manipulation of the color channel for example by actuating a hand or foot switch and also to manually terminate the manipulation, for example by actuating the same switch again or by actuating another switch. If the electronic manipulation is activated and terminated manually, it is however possible, in contrast to automated activation and termination of the electronic manipulation, that the electronic manipulation in the time periods between the laser pulses is not interrupted due to the quick pulse sequence of the coagulation laser 1.

In the present exemplary embodiment, the laser-surgical apparatus includes a warning module 13, which issues an alert if the manipulation module 9 is active without having received a switch-on signal from the communication module 11. Said warning module 13, which in the present exemplary embodiment is part of the graphics module 7 and, like the graphics module 7, is implemented as a software module or as a hardware module, integrates an alert into the color image presented on the monitor 8, for example in the form of a boundary designed to be easily perceivable or in the form of an indication of the active manipulation that is easy to perceive in the peripheral region of the color image, if the graphics module 7 has not received a switch-on signal from the communication module 11, but receives electronically manipulated pieces of image information from the manipulation module 9.

The described electronic manipulations of the pieces of image information and of the color presentation on the monitor 8 can be performed, for example, on a computer or on a hardware or software module of the laser-surgical apparatus that is specifically provided therefor. In addition, the method can also be performed on a hardware or software module of the surgical microscope 5 that is specifically provided therefor.

Figure 3:
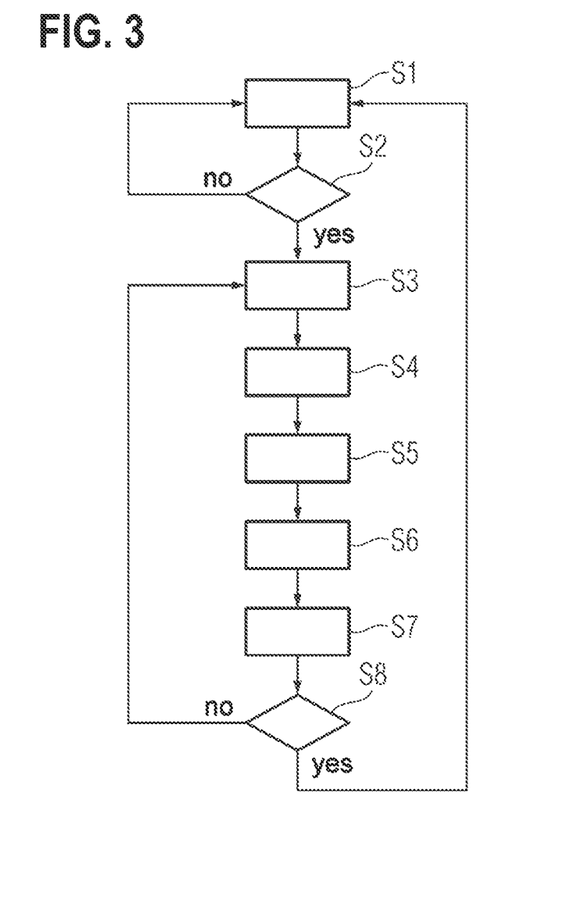
FIG. 3 shows a flowchart of the method for suppressing stray light in a color image recorded with a digital image sensor or with a plurality of digital image sensors according to an exemplary embodiment of the disclosure.

The method steps performed by the graphics module 7 and the manipulation module 9 for suppressing the stray-light-forming laser light are illustrated in FIG. 3 in the form of a flowchart. The performance of the illustrated method steps can be initiated, for example, as in the exemplary embodiment described below, by way of corresponding instructions of a computer program that is executed on a computer. The computer program can be stored on a non-volatile, computer-readable storage medium and be loaded therefrom into the computer. Alternatively, the computer program can also be loaded onto the computer via a local network or via the Internet. If the method is performed in a hardware module that is specifically provided for performing the method, the instructions for performing the method can also be stored in a read-only memory of this module.

After the start of the computer program with the instructions for performing the method, the method is in a wait state step S1, from which it starts an interrogation at specific time intervals (step S2) as to whether or not a switch-on signal is present. If, in the process, it is established that there is no switch-on signal, the method returns to the wait state (step S1). On the other hand, if it is established in step S2 that a switch-on signal is present, the method moves on to step S3, in which the manipulation module 9 receives pieces of image information from the digital image sensor. Said pieces of image information contain separate pieces of image information for a number of color channels, in the present exemplary embodiment for a red, a green, and a blue color channel. After the receipt of the pieces of image information, the method moves on to step S4, in which the pieces of image information of the green color channel are removed from the totality of the pieces of image information. Next, in step S5, the pieces of image information of the green color channel that have been removed are replaced by a copy of the pieces of image information of the blue color channel. The pieces of image information thus prepared are then transmitted, in step S6, to the graphics module 7, which generates from the separate pieces of image information of the color channels a color image (step S7), which is transmitted for presentation to the monitor 8, wherein a color adaptation, as was described in the context of the laser-surgical apparatus, may be performed as part of step S7. After the color image has been sent to the monitor 8, an interrogation as to whether a switch-off signal is present is performed in step S8. If no switch-off signal is present, the method returns to step S3, where new pieces of image information are received. Otherwise, the method returns to the wait state in step S1.

The present disclosure has been described in detail on the basis of exemplary embodiments. However, it is possible to deviate from these exemplary embodiments. For example, the exemplary embodiments illustrate the graphics module 7 and the manipulation module 9 as separate modules. However, the manipulation module 9 can also be a submodule of the graphics module 7 and, in the case of a software module, for example be a subroutine of the graphics module 7. In addition, the surgical microscope 5 in the present exemplary embodiment is equipped with a binocular viewing unit. However, it may also be embodied exclusively for viewing the image that has been acquired with the microscope on the monitor 8. In addition, the method according to the disclosure can also be used in other apparatuses in which very intensive stray light occurs. Accordingly, it is not necessarily required to electronically manipulate the green color channel but rather the color channel having the greatest overlap with the spectral wavelength distribution of the stray light. Therefore, the present disclosure is not intended to be limited by the exemplary embodiments but rather only by the appended claims.

Possible variants for the set-up of a surgical microscope 5, as can be used in the described exemplary embodiment of the laser-surgical apparatus, will be described below with reference to FIGS. 4 and 5. The ophthalmic loupe 6 and the optics assembly 10 and also the intermediate image plane 12 are here not illustrated in FIGS. 4 and 5.

Figure 4:
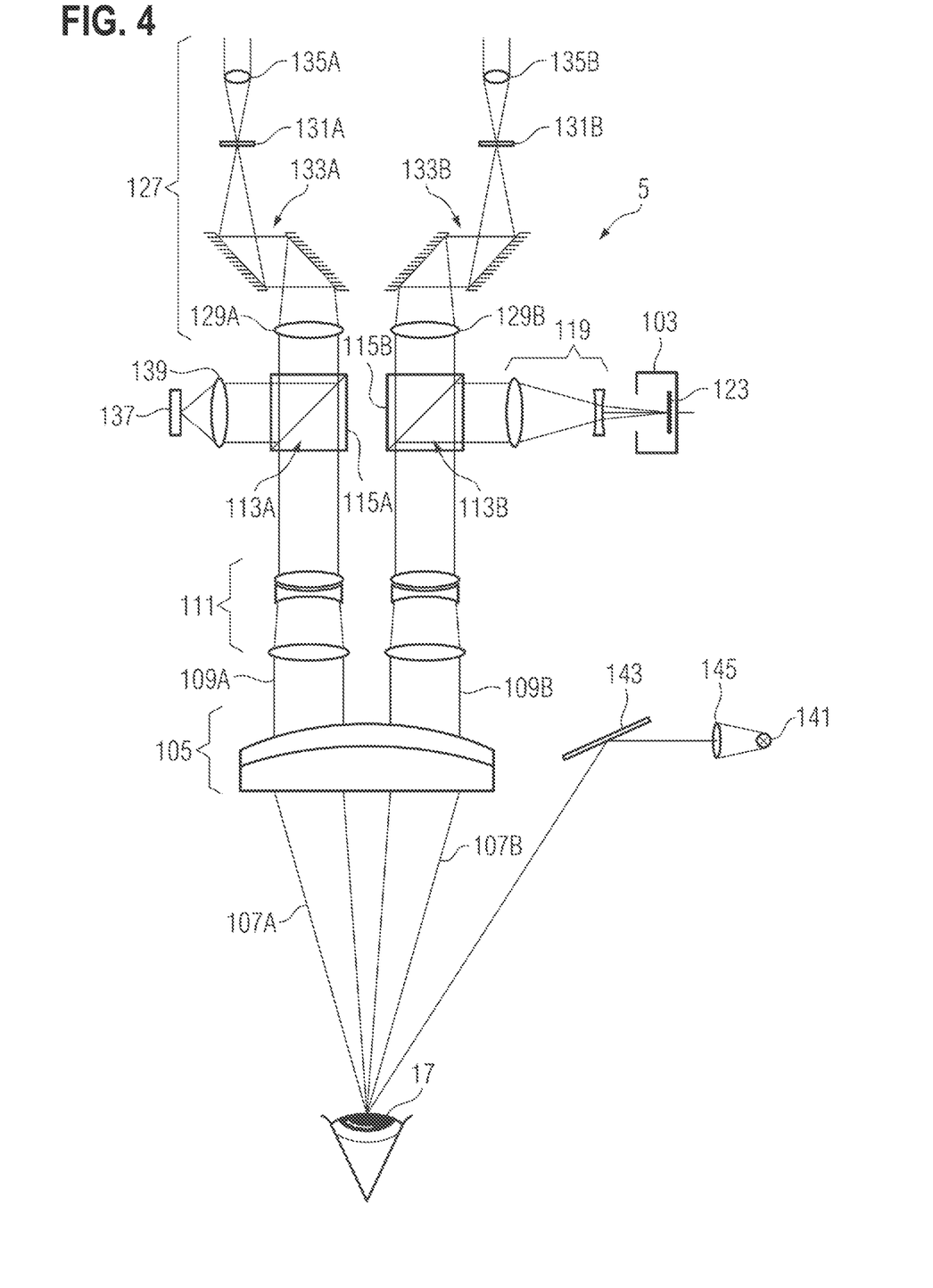
FIG. 4 shows a schematic illustration of the set-up of a surgical microscope.

The surgical microscope 5 shown in FIG. 4 includes, as essential components, an objective 105 that should face an object field 17, said objective, in particular, being able to be embodied as an achromatic or apochromatic objective. The object field 17 in the present exemplary embodiment is an eye, and in particular the retina of an eye. In the present exemplary embodiment, the objective 105 consists of two partial lenses that are cemented to one another and form an achromatic objective. The object field 17 is arranged in the focal plane of the objective 105 such that it is imaged at infinity by the objective 105. Expressed differently, a divergent beam 107A, 107B emanating from the object field 17 is converted into a parallel beam 109A, 109B during its passage through the objective 105.

A magnification changer 111 is arranged on the observer side of the objective 105, which magnification changer can be embodied either as a zoom system for changing the magnification factor in a continuously variable manner as in the illustrated exemplary embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors, and which can be introduced into the beam path alternately. Both a zoom system and a Galilean changer convert an object-side parallel beam into an observer-side parallel beam having a different beam diameter. In the present exemplary embodiment, the magnification changer 111 is already part of the binocular beam path of the surgical microscope 5, i.e., it has a dedicated lens combination for each stereoscopic partial beam path 109A, 109B of the surgical microscope 5. In the present exemplary embodiment, a magnification factor is adjusted with the magnification changer 111 by way of a motor-driven actuator which, together with the magnification changer 111, is part of a magnification changing unit for adjusting the magnification factor.

The magnification changer 111 is adjoined on the observer side by an interface arrangement 113A, 113B, with which external devices can be connected to the surgical microscope 11 and which includes beam splitter prisms 115A, 115B in the present exemplary embodiment. However, in principle, use can also be made of other types of beam splitters, for example partly transmissive mirrors. In the present exemplary embodiment, the interfaces 113A, 113B serve to output couple a beam from the beam path of the surgical microscope 5 (beam splitter prism 115B) and to input couple a beam into the beam path of the surgical microscope 5 (beam splitter prism 115A).

In the present exemplary embodiment, the beam splitter prism 115A in the partial beam path 109A serves to reflect information or data for an observer into the partial beam path 109A of the surgical microscope 5 with the aid of a display 37, for example a digital mirror device (DMD) or an LCD display, and an associated optical unit 139 by way of the beam splitter prism 115A. A camera adapter 119 with a digital color camera 103 secured thereto, said camera being equipped with at least one digital image sensor 123, for example with at least one charge-coupled device (CCD) sensor or at least one complementary metal-oxide-semiconductor (CMOS) sensor, is arranged at the interface 113B in the other partial beam path 109B. It is possible with the digital color camera 103 to record a digital image of the object field 17. The color camera 103 can either have a single image sensor with a Bayer matrix arranged upstream or a color splitter system with color splitter prisms and three separate image sensors without a Bayer matrix.

The interface 113 is followed on the observer side by a binocular tube 127. The latter has two tube objectives 129A, 129B, which focus the respective parallel beam 109A, 109B onto an intermediate image plane 131, i.e., image the object field 17 onto the respective intermediate image plane 131A, 131B. The intermediate images situated in the intermediate image planes 131A, 131B are finally imaged at infinity in turn by eyepiece lenses 135A, 135B, such that an observer can observe the intermediate image with a relaxed eye. Moreover, the distance between the two partial beams 109A, 109B is increased in the binocular tube with a mirror system or with prisms 133A, 133B in order to adapt said distance to the interocular distance of the observer. In addition, image erection is carried out by the mirror system or the prisms 133A, 133B. If required, a laser safety filter can be introduced between the interface 113 and the binocular tube 127, although said filter does not influence the beam path extending to the digital color camera 103.

The surgical microscope 5 is additionally equipped with an illumination apparatus, with which the object field 17 can be illuminated with broadband illumination light. To this end, the illumination apparatus in the present exemplary embodiment has a white-light source 141, for example a halogen lamp or a gas discharge lamp. The light emanating from the white-light source 141 is directed in the direction of the object field 17 via a deflection mirror 143 or a deflection prism in order to illuminate said field. Furthermore, an illumination optical unit 145 is present in the illumination apparatus, said illumination optical unit ensuring uniform illumination of the entire observed object field 17.

Reference is made to the fact that the illumination beam path illustrated in FIG. 4 is highly schematic and does not necessarily reproduce the actual course of the illumination beam path. In principle, the illumination beam path can be embodied as what is known as oblique illumination, which comes closest to the schematic illustration in FIG. 4. In the case of such oblique illumination, the beam path extends at a relatively large angle (6° or more) with respect to the optical axis of the objective 105 and, as illustrated in FIG. 4, may extend completely outside the objective 105. Alternatively, however, there is also the possibility of allowing the illumination beam path of the oblique illumination to extend through a marginal region of the objective 105. A further possibility for the arrangement of the illumination beam path is what is known as 0° illumination, in which the illumination beam path extends through the objective 105 and is input coupled into the objective 105 between the two partial beam paths 109A, 109B, along the optical axis of the objective 105 in the direction of the object field 17. Finally, it is also possible to embody the illumination beam path as what is known as coaxial illumination, in which a first illumination partial beam path and a second illumination partial beam path are present. The partial beam paths are coupled into the surgical microscope 11 via one or more beam splitters parallel to the optical axes of the observation partial beam paths 109A, 109B, such that the illumination extends coaxially with respect to the two observation partial beam paths.

In the exemplary embodiment of the surgical microscope 5 shown in FIG. 4, the objective 105 consists only of one achromatic lens. However, use can also be made of an objective lens system composed of a plurality of lenses, in particular what is known as a varioscope objective, with which it is possible to vary the working distance of the surgical microscope 5, i.e., the distance between the object-side focal plane and the vertex of the first object-side lens surface of the objective 105, also referred to as front focal distance. The object field 17 arranged in the focal plane is imaged at infinity by a varioscope objective, too, and so a parallel beam is present on the observer side.

Figure 5:
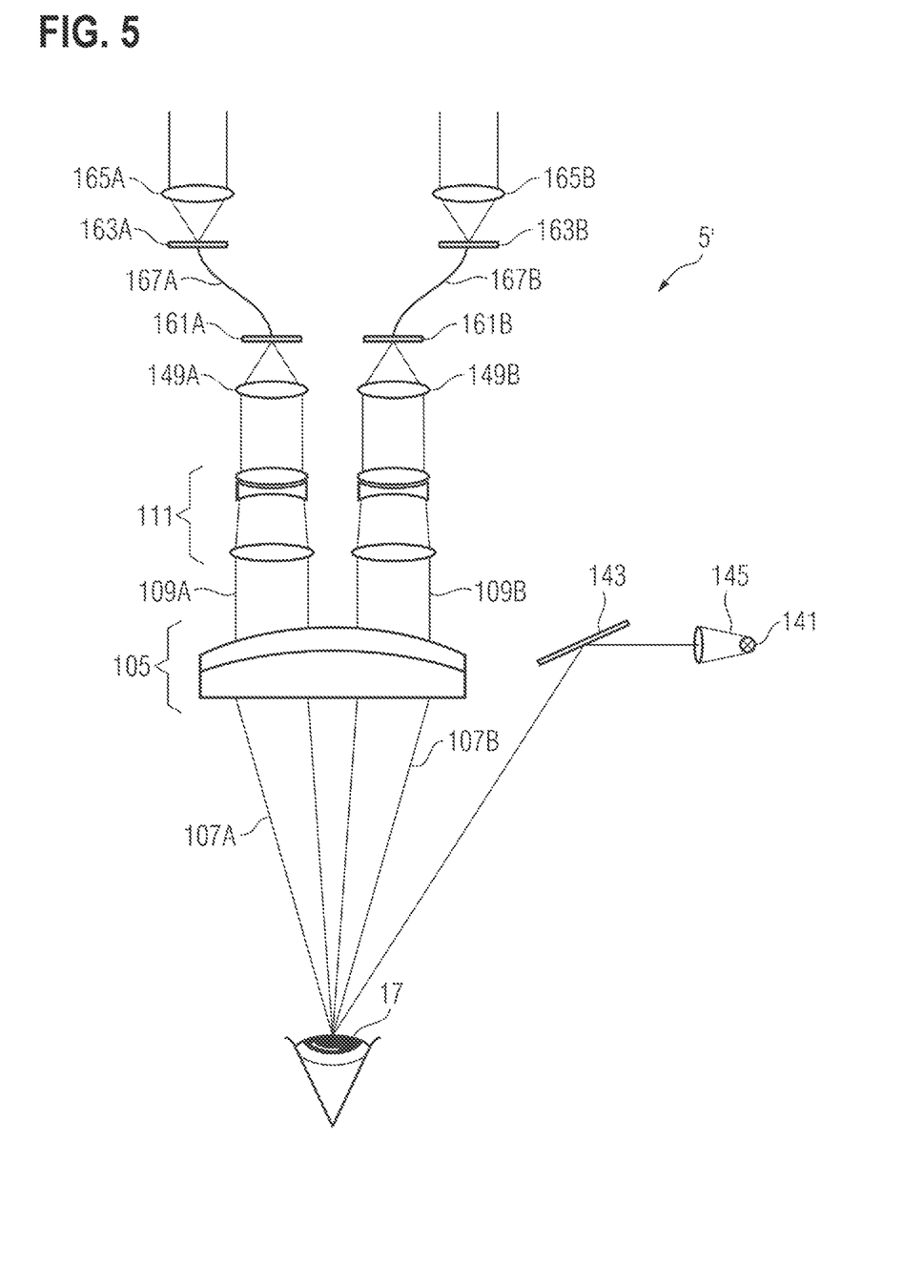
FIG. 5 shows a schematic illustration of an alternative set-up of a surgical microscope.

FIG. 5 shows a schematic illustration of one example of a purely digital surgical microscope 5'. In this surgical microscope, the main objective 105, the magnification changer 111, and the illumination system 141, 143, and 145 do not differ from the surgical microscope 5 with the optical viewing unit that is illustrated in FIG. 4. The difference lies in the fact that the surgical microscope 5' shown in FIG. 5 does not include an optical binocular tube. Instead of the tube objectives 129A, 129B shown in FIG. 4, the surgical microscope 5' shown in FIG. 5 includes focusing lenses 149A, 149B, with which the binocular observation beam paths 109A, 109B are imaged onto digital image sensors 161A, 161B. Here, the digital image sensors 161A, 161B can be, for example, CCD sensors or CMOS sensors. The images recorded by the image sensors 161A, 161B are transmitted digitally to digital displays 163A, 163B, which may be embodied as LED displays, as LCD displays or as displays based on organic light-emitting diodes (OLEDs). As in the present example, eyepiece lenses 165A, 165B can be assigned to the displays 163A, 163B, with which lenses the images presented on the displays 163A, 163B are imaged at infinity such that a viewer can view said images with relaxed eyes. The displays 163A, 163B and the eyepiece lenses 165A, 165B can be part of a digital binocular tube; however, they can also be part of a head mounted display (HMD) such as, e.g., a pair of smartglasses. Additionally or alternatively, the images recorded with the digital image sensors 161A, 161B can also be presented on a monitor 8, as is shown in FIG. 1. The digital image sensors 161A, 161B in the present exemplary embodiment are provided in each case with a Bayer matrix. Alternatively, however, it is also possible for in each case three digital image sensors and one color splitter system, which supplies different color channels to the three image sensors, to be present per stereo channel.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Coagulation laser
2 Trocar
3 Target laser
4 Optical fiber
5 Surgical microscope
6 Ophthalmic loupe
7 Graphics module
8 Monitor
9 Manipulation module
10 Optics group 11 Communication module
12 Intermediate image plane
13 Warning module
17 Object field
105 Objective
107 A, B Divergent beam
109 A, B Parallel beam
111 Magnification changer
113 A, B Interface arrangement
115 A, B Beam splitter prism
119 Camera adapt
123 Image sensor
127 Binocular tube
129 A, B Tube objective
131 A, B Intermediate image plane
133 A, B Prism
135 A, B Eyepiece lens
137 Display
139 Optics
141 White-light source
143 Deflection mirror
145 Illumination optical unit
148 Surgical microscope
149 A, B Focusing lens
161 A, B Image sensor
163 A, B Display
165 A, B Eyepiece lens
167 A, B Cable
S1 Wait state
S2 Interrogation as to whether or not a switch-on signal is present
S3 Receipt of pieces of image information
S4 Removal of pieces of image information
S5 Replacing pieces of image information
S6 Transmission of pieces of image information to graphics module
S7 Generating color image
S8 Interrogation as to whether or not a switch-off signal is present

What is claimed is:

1. A method for suppressing stray light with a narrowband wavelength distribution in a color image, the stray light being recorded with a digital image sensor or a plurality of digital image sensors, the method comprising:
separately recording, by the digital image sensor or by the digital image sensors, different color channels that represent mutually different spectral wavelength distributions with in each case one maximum corresponding to a specific spectral color;
producing separate pieces of image information for the color channels;
generating the color image by combining the separate pieces of image information; and
suppressing the stray light by electronically manipulating the pieces of image information of the color channel a spectral wavelength distribution of which has the greatest overlap with the narrowband wavelength distribution of the stray light before the combining of the separate pieces of image information or during the combining of the separate pieces of image information.

2. The method according to claim 1, wherein electronically manipulating the pieces of image information comprises:
not including the pieces of image information of the color channel in the color image whose spectral wavelength distribution has the largest overlap with the narrowband wavelength distribution of the stray light, or
including the pieces of image information of the color channel in the color image whose spectral wavelength distribution has the largest overlap with the narrowband wavelength distribution of the stray light with a reduced weighting compared to the pieces of image information of the remaining color channels, when the color image is generated.

3. The method according to claim 1, wherein electronically manipulating the pieces of image information comprises at least partially replacing the pieces of image information of the color channel the spectral wavelength distribution of which has the largest overlap with the narrowband wavelength distribution of the stray light with pieces of image information of at least one of the remaining color channels.

4. The method according to claim 1, wherein electronically manipulating the pieces of image information comprises assigning the pieces of image information of at least one of the color channels a color that deviates from the color corresponding to the maximum of its spectral wavelength distribution when the color image is generated.

5. The method according to claim 1, wherein:
the narrowband wavelength distribution of the stray light has a maximum in a green wavelength range,
the different color channels comprise at least three color channels, wherein a first one of the color channels is a red color channel the spectral wavelength distribution of which has a maximum representing a red color, a second one of the color channels is a green color channel the spectral wavelength distribution of which has a maximum representing a green color, and a third one of the color channels is a blue color channel the spectral wavelength distribution of which has a maximum representing a blue color, and
the pieces of image information of the green color channel are electronically manipulated.

6. The method according to claim 5, wherein electronically manipulating the pieces of image information comprises at least one of:
not including the pieces of image information in the green color channel in the color image, or including the pieces of image information in the green color channel in the color image with a reduced weighting compared to the pieces of image information of the red color channel and the blue color channel, during the generating of the color image,
replacing the pieces of image information of the green color channel at least partially by pieces of image information of the blue color channel, and
assigning the pieces of image information of at least the red color channel or the blue color channel a color that deviates from the red or blue color represented by the maximum of the respective spectral wavelength distribution during the generation of the color image.

7. The method according to claim 1, wherein an alert is issued at least when an electronic manipulation of the pieces of image information is active and the stray light is not present.

8. A laser-surgical apparatus comprising:
a laser emitting laser light with a narrowband wavelength distribution;
a digital image sensor or a plurality of digital image sensors configured to separately record different color channels that represent mutually different spectral wavelength distributions with in each case one maximum corresponding to a specific spectral color and to produce separate pieces of image information for individual color channels;

a graphics module configured to combine the separate pieces of image information into one color image; and a manipulation module configured to suppress the laser light in the color image, which makes it possible to electronically manipulate the pieces of image information of the color channel the spectral wavelength distribution of which has a largest overlap with the narrowband wavelength distribution of the laser light before the separate pieces of image information are combined or when the separate pieces of image information are combined.

9. The laser-surgical apparatus according to claim 8, wherein the manipulation module configured to suppress the laser light is configured to electronically manipulate the pieces of image information such that at least one of:

the pieces of image information of the color channel the spectral wavelength distribution of which has the largest overlap with the narrowband wavelength distribution of the laser light are not included at all in the color image, or are included in the color image with a reduced weighting compared to the pieces of image information of the remaining color channels, when the color image is generated, the pieces of image information of the color channel the spectral wavelength distribution of which has the largest overlap with the narrowband wavelength distribution of the laser light are at least partially replaced with pieces of image information of at least one of the remaining color channels, and the pieces of image information of at least one of the color channels are assigned a color that deviates from the color corresponding to the maximum of its spectral wavelength distribution, when the color image is generated.

10. The laser-surgical apparatus according to claim 8, further comprising:

a communication module connected at least to the laser and to the manipulation module and configured to transmit a switch-on signal to the manipulation module when the laser is switched on, and wherein the manipulation module is configured to begin the electronic manipulation of the pieces of image information upon receipt of the switch-on signal.

11. The laser-surgical apparatus according to claim 10, wherein:

the communication module is additionally configured to transmit a switch-off signal to the manipulation module when the laser is switched off, and the manipulation module is configured to terminate the electronic manipulation of the pieces of image information upon receipt of the switch-off signal, or the communication module is additionally configured to transmit a switch-on duration to the manipulation model in addition to the switch-on signal, wherein the switch-on duration indicates how long the laser remains switched on once it has been switched on, and the manipulation module is configured to terminate the electronic manipulation of the pieces of image information after the switch-on duration has expired.

12. The laser-surgical apparatus according to claim 10, wherein:

the communication module is connected to the graphics module and is configured to transmit the switch-on signal and, if present, the switch-off signal or the switch-on duration to the graphics module, and the graphics module is configured to begin the deviating assignment of the color upon receipt of the switch-on signal and, if a switch-on duration or a switch-off signal is transmitted, to terminate the deviating assignment of the color after the switch-on duration has expired or upon receipt of the switch-off signal.

13. The laser-surgical apparatus according to claim 8, further comprising a warning module, which issues an alert at least when the manipulation module is active and the laser is not active.

14. An optical observation device comprising:

a digital image sensor or a plurality of digital image sensors configured to separately record different color channels that represent mutually different spectral wavelength distributions with in each case one maximum corresponding to a specific spectral color and to produce separate pieces of image information for the individual color channels;

a graphics module configured to combine the separate pieces of image information into one color image; and a manipulation module configured to suppress stray light with a narrowband wavelength distribution in a color image, which makes it possible to electronically manipulate the pieces of image information of the color channel the spectral wavelength distribution of which has the largest overlap with the narrowband wavelength distribution of the stray light before the pieces of image information are combined or when the pieces of image information are combined.

15. The optical observation device according to claim 14, wherein the manipulation module configured to suppress the stray light is configured to electronically manipulate the pieces of image information such that at least one of:

the pieces of image information of the color channel the spectral wavelength distribution of which has the largest overlap with the narrowband wavelength distribution of the stray light are not included at all in the color image, or are included in the color image with a reduced weighting compared to the pieces of image information of the remaining color channels, when the color image is generated, the pieces of image information of the color channel the spectral wavelength distribution of which has the largest overlap with the narrowband wavelength distribution of the stray light are at least partially replaced with pieces of image information of at least one of the remaining color channels, and the pieces of image information of at least one of the color channels are assigned a color that deviates from the color corresponding to the maximum of its spectral wavelength distribution, when the color image is generated.

* * * * *

UNITED STATES PATENT AND TRADEMARK OFFICE
CERTIFICATE OF CORRECTION

PATENT NO. : 11,974,949 B2
APPLICATION NO. : 17/405901
DATED : May 7, 2024
INVENTOR(S) : Frank Keib, Christian Beder and Peter Reimer Page 1 of 1

It is certified that error appears in the above-identified patent and that said Letters Patent is hereby corrected as shown below:

In the Specification

For BACKGROUND, Column 1:
Line 57: Replace "1×10-4" with "$1 \times 10^{-4}$"

For LIST OF REFERENCE NUMERALS, Column 19:
Line 11: Replace "Camera adapt" with "Camera adapter"

Signed and Sealed this
Twenty-fourth Day of September, 2024

Katherine Kelly Vidal
*Director of the United States Patent and Trademark Office*